US00PP12382P2

(12) United States Plant Patent
Drewlow

(10) Patent No.: US PP12,382 P2
(45) Date of Patent: Feb. 5, 2002

(54) KALANCHOE PLANT NAMED 'FOREVER MAXI ANTIQUE PINK'

(75) Inventor: Lyndon W. Drewlow, County Santa Barbara, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/566,672

(22) Filed: May 8, 2000

(51) Int. Cl.[7] ..... A01H 5/00

(52) U.S. Cl. ..... Plt./339

(58) Field of Search ..... Plt./339

*Primary Examiner*—Bruce R. Campell
*Assistant Examiner*—Michelle Kizilkaya
(74) *Attorney, Agent, or Firm*—Webb Ziesenheim Logsdon Orkin & Hanson, P.C.

(57) ABSTRACT

A new Kalanchoe cultiver named 'Forever Maxi Antique Pink' characterized by its large deep pink colored flowers, large leaves, semi-upright and tall growth habit and excellent basal branching.

1 Drawing Sheet

The present invention relates to a new and distinct cultivar of Kalanchoe plant, botanically known as *Kalanchoe blossfeldiana*, and known by the cultivar name 'Forever Maxi Antique Pink'. 'Forever Maxi Antique Pink' was developed in a controlled breeding program in Ashtabula, Ohio by crossing Mikkelsen Seedling No. 90-298-1 (seed parent) (unpatented) with Mikkelsen Seedling No. 91-148-3 (pollen parent) (unpatented). The seed and pollen parents are proprietary breeding lines which have not been sold or made publicly available in this country. The plant is perennial but typically used as an annual in the floriculture industry.

Asexual reproduction by stem cuttings taken by the inventor in Lompoc, Calif. has shown that the unique features of this new Kalanchoe are stabilized and are reproduced true to type in successive propagations.

The following characteristics distinguish the new Kalanchoe from other cultivated Kalanchoes of this type known to the inventor. The characteristics are described with comparative reference to the cultivars Baluran (unpatented) and Kerinci (U.S. Plant Pat. No. 10,031).

1. 'Forever Maxi Antique Pink' has flowers colored deep pink of Red Group 55A while 'Baluran' has paler colored flowers of Red-Purple Group 57D and 'Kerinci' has flowers between Pink Groups 66C and 66D.

2. 'Forever Maxi Antique Pink' is taller at 18 cm than 'Baluran' at 16 cm and 'Kerinci' at 14 cm.

3. 'Forever Maxi Antique Pink' has larger flowers at 16 mm in diameter while 'Baluran' and 'Kerinci' each have flowers of 14 mm in diameter.

4. 'Forever Maxi Antique Pink' has larger leaves (9 to 10 cm long) than each of 'Baluran' and 'Kerinci' (8 to 9 cm long).

5. 'Forever Maxi Antique Pink' has a cyme inflorescence while 'Baluran' and 'Kerinci' each have a compound umbel type of inflorescence.

6. 'Forever Maxi Antique Pink' has thicker stronger primary and secondary peduncles than each of 'Baluran' and 'Kerinci'.

The accompanying colored photograph illustrates the overall appearance of this cultivar, as described in detail below, taken as a face view of the plant and showing the colors as true as it is reasonably possible to obtain in a colored reproduction of this type.

The following is a detailed description of the new cultivar, based on plants produced in greenhouses in Lompoc, Calif. during the Winter season of the year. Plants were grown in 10 cm pots and measurements were taken 13 weeks after rooted cuttings were planted. Height measurements were taken from the soil line of the container. The plants were grown at 16° C. night temperatures, 3000–4000 foot candles of light, and 200 ppm nitrogen, 75 ppm potassium, and 200 ppm phosphorous nutritional levels, with trace elements added. Habit of growth, foliage coloration, size of leaves, and peduncle length will be greatly influenced by nutritional and environmental conditions.

Color references are made to The Royal Horticultural Society Colour Chart except where general terms of ordinary dictionary significance are used.

Parentage: A controlled cross between female parent Mikkelsen Seedling No. 90-298-1 and male parent Mikkelsen Seedling No. 91-148-3.

Propagation:

(*A*) *Type cutting.*—Stem tip cuttings up to 3 cm long.

(*B*) *Time to root.*—10 days at 21° C. summer; 12 days at 21° C. winter.

(*C*) *Rooting habit.*—Fine, fibrous, abundant.

Plant description:

*Habit and form of growth.*—Semi-tall, semi-mounded, excellent basal branching; flower clusters bloom above foliage. Environment and use of growth regulators will play a role in final height. Average height is 25 cm and average width is 25 cm. Internode length is typically 15 mm. Main stem diameter is 10 mm, stem texture is smooth, glabrous, and stem color is Yellow-Green Group 147A.

*Foliage description.*—Leaves simple and opposite. Leaves are petiolate and petioles are Yellow-Green Group 147A having a length of 16 mm and a width of 5 mm. Size: Average, full grown leaves on a plant when grown in a 10 cm pot are 9 to 10 cm long and 6 to 6.5 cm wide. Shape: Ovate with obtuse apex and acute base. Texture: Glabrous; coriaceous and succulent. Margin: Crennate; shallow lobed. Color: Young foliage top side is Green Group 137A, underside is Yellow-Green Group 146A; mature foliage top side is Yellow-Green Group 147A, underside is between Yellow-Green Groups 147A and 147B.

*Branching.*—Average number of lateral branches is 8. The average lateral branch length is 20 cm and average lateral branch diameter is 5 mm. The branch texture is smooth, glabrous and color is Yellow-Green Group 147A.

Flowering description:

*Flowering habits.*—Inflorescence is a compound dichasial cyme. Terminal flower on main axis opens first followed by the terminal flowers of the side branches, continuing with the subsequent development of branches in the inflorescence. Inflorescence is made up of the main stem and up to 8 or more lateral branches depending on growing schedule followed.

*Natural flowering season.*—Early January. Flowering time under controlled daylength (10 hours daylight, 14 hours darkness) at 20° C. in summer is 8.5 to 9 weeks; in winter is 10 to 10.5 weeks. Flowering time depends on temperature, light intensity and other growing conditions.

*Flower buds.*—Oblong, up to 12 mm long before showing color, developing to tubular as flower petals mature; sheathed in four (4) sepals colored Yellow-Green Group 144A. Sepals are individual with a lanceolate shape. Sepals are 8 mm long and 2 mm wide.

*Flowers borne.*—Compound dichasial cyme with primary peduncle being 5 mm in diameter just below the first branch of the inflorescence; length of peduncle will vary depending on growing conditions. The average number of peduncles is 10 with an average length of 16 cm, average diameter of 5 mm, smooth, glabrous texture, and Yellow-Green Group 147A color. The average number of pedicels is 250 with an average length of 3 mm, average diameter of 1 mm, smooth, glabrous texture, and Yellow-Green Group 147A color. Pedicels vary in length depending on where they are in the inflorescence. Flowers are 16 mm in diameter.

*Quantity of flowers.*—Numerous long-lasting flowers on the main stem plus the 8 or more lateral branches will have 30 or more flowers each. Approximate time period for bloom lastingness is 4 to 6 weeks. The florets are flat in shape.

*Petals.*—Shape: Almost rounded, top cuspidate. Color: Top side when opening is Red Group 43C, fading to Red Group 55A. Underside is Red Group 55 B at petal edge and Red Group 55D at center of petal. Number of petals: 4. Size: Individual petals are 7 mm wide and 8 mm long.

*Reproductive organs.*—Stamens: 8 in number, with an average size of 3 mm not fused to the petal. Anthers: Flat, elliptical in shape, yellow-green in color. Filament color: Yellow-green. Pollen: Abundant, yellow. Pistils: Average of 4 per flower with an average size of 12 mm. Stigma: Flat in shape, mature color is white. Style color: Green. Ovaries: 4 in number, size 7 mm when immature, color green.

*Fertility.*—The plants are fertile, but do not normally set seed under greenhouse or garden conditions, unless in a controlled crossing program.

Disease resistance: 'Forever Maxi Antique Pink' has shown resistance to powdery mildew. No disease problems have been observed to date.

OTHER IMPORTANT CHARACTERISTICS

1. Semi-tall growth combined with good lateral and basal branching allows cultivars to be finished in a 15 cm pot from one cutting instead of the usual three cuttings.

2. Excellent flower coverage on upper half of plant due to excellent lateral and basal branching.

3. No or minimum use of growth regulators needed to grow this cultivar.

4. Pinching is not required or recommended.

I claim:

1. A new and distinct cultivar of Kalanchoe plant named 'Forever Maxi Antique Pink', as illustrated and described.

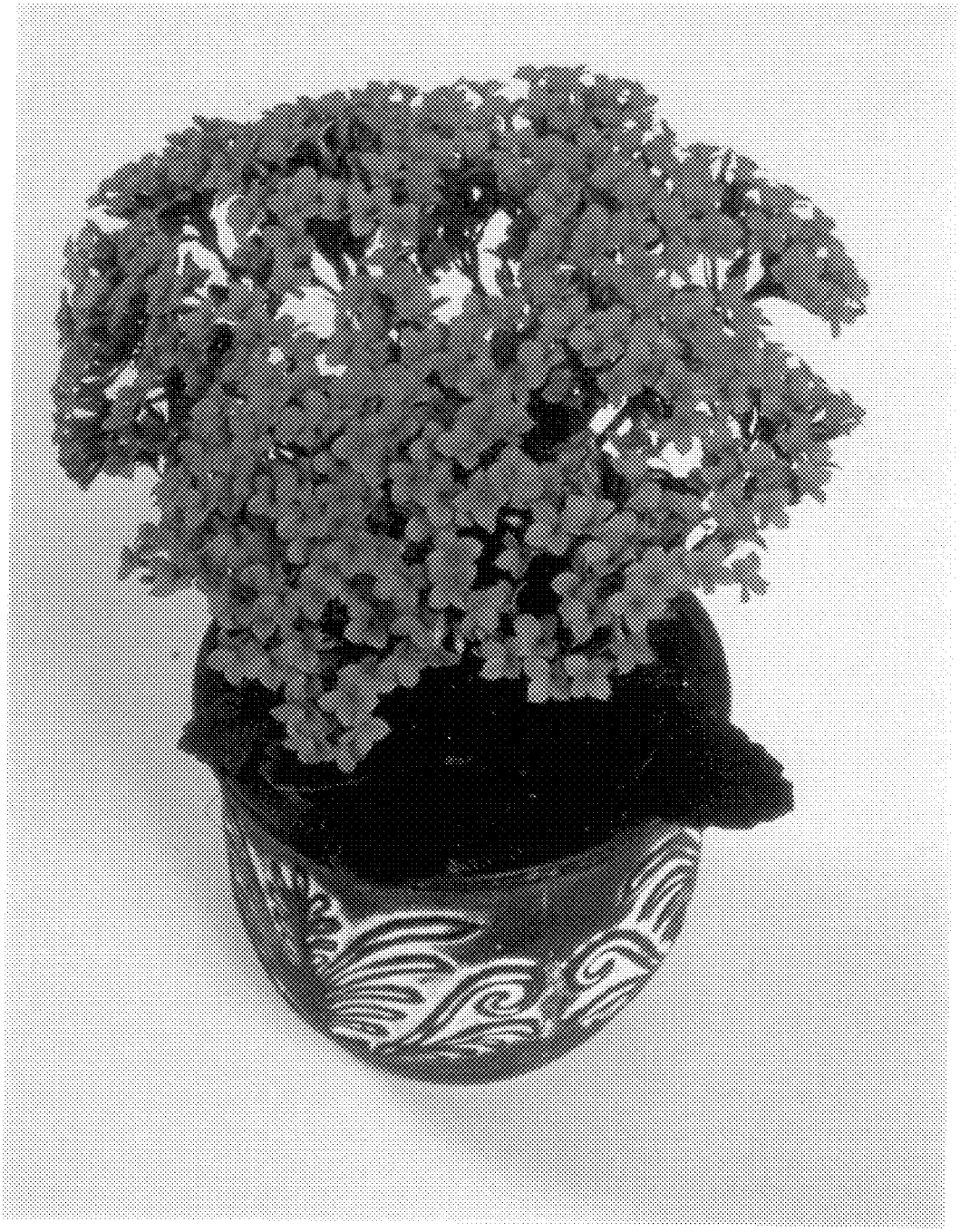

* * * * *